US012673218B2

(12) United States Patent
Beltran et al.

(10) Patent No.: US 12,673,218 B2
(45) Date of Patent: Jul. 7, 2026

(54) DOWNSTREAM VARIABLE THICKNESS ENERGY SELECTION SYSTEM FOR CHARGED PARTICLE THERAPY

(71) Applicant: Mayo Foundation for Medical Education and Research, Rochester, MN (US)

(72) Inventors: Chris J. Beltran, Ponte Vedra Beach, FL (US); Keith M. Furutani, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 728 days.

(21) Appl. No.: 18/004,160

(22) PCT Filed: Jul. 2, 2021

(86) PCT No.: PCT/US2021/040358
§ 371 (c)(1),
(2) Date: Jan. 3, 2023

(87) PCT Pub. No.: WO2022/093340
PCT Pub. Date: May 5, 2022

(65) Prior Publication Data
US 2023/0264041 A1 Aug. 24, 2023

Related U.S. Application Data

(60) Provisional application No. 63/106,266, filed on Oct. 27, 2020.

(51) Int. Cl.
*A61N 5/10* (2006.01)

(52) U.S. Cl.
CPC ........ *A61N 5/10* (2013.01); *A61N 2005/1087* (2013.01); *A61N 2005/1095* (2013.01)

(58) Field of Classification Search
CPC .............. A61N 5/10; A61N 2005/1087; A61N 2005/1095
(Continued)

(56) References Cited

U.S. PATENT DOCUMENTS

2003/0136924 A1    7/2003   Kraft et al.
2004/0149934 A1    8/2004   Yanagisawa et al.
(Continued)

FOREIGN PATENT DOCUMENTS

WO        2007021226 A1    2/2007

OTHER PUBLICATIONS

PCT International Search Report and Written Opinion, PCT/US2021/040358, Dec. 20, 2021, 19 pages.
(Continued)

*Primary Examiner* — Michael Maskell
(74) *Attorney, Agent, or Firm* — Quarles & Brady LLP

(57) ABSTRACT

A variable thickness energy selection system for use in a charged particle therapy system is arranged within the nozzle housing downstream of monitoring systems, such as a dose monitor and spot position monitor. This positions the energy selection system proximal to the patient. The thickness of an absorber within the energy selection system can be varied quickly without requiring the ion beam to be turned off between energy selections, thereby allowing for rapid control of the energy selection of the ion beam. The absorber may include one or more high density solid absorbers, or a high-density liquid absorber contained in a closed fluid dynamic system that includes an enclosure positioned within the beam path and a reservoir positioned outside of the beam path.

29 Claims, 7 Drawing Sheets

(58) Field of Classification Search
USPC ........................................... 250/492.1–492.3
See application file for complete search history.

(56) References Cited

U.S. PATENT DOCUMENTS

| 2004/0200983 | A1* | 10/2004 | Fujimaki ................... | A61N 5/10 |
| | | | | 250/492.3 |
| 2008/0260098 | A1* | 10/2008 | Al-Sadah ............. | A61N 5/1042 |
| | | | | 378/65 |
| 2009/0242789 | A1 | 10/2009 | Tachikawa | |
| 2012/0316378 | A1* | 12/2012 | Torikai ................... | G21K 1/093 |
| | | | | 600/1 |
| 2013/0221213 | A1 | 8/2013 | Takayanagi et al. | |
| 2015/0031933 | A1* | 1/2015 | Yamamoto ........... | A61N 5/1048 |
| | | | | 600/1 |
| 2017/0281981 | A1* | 10/2017 | Mansfield ............. | A61N 5/1043 |
| 2020/0298025 | A1* | 9/2020 | Cooley, III .......... | A61N 5/1079 |

OTHER PUBLICATIONS

European Patent Office, Extended Search Report, Application No. 25220174.4, Feb. 11, 2026, 6 pages.

* cited by examiner

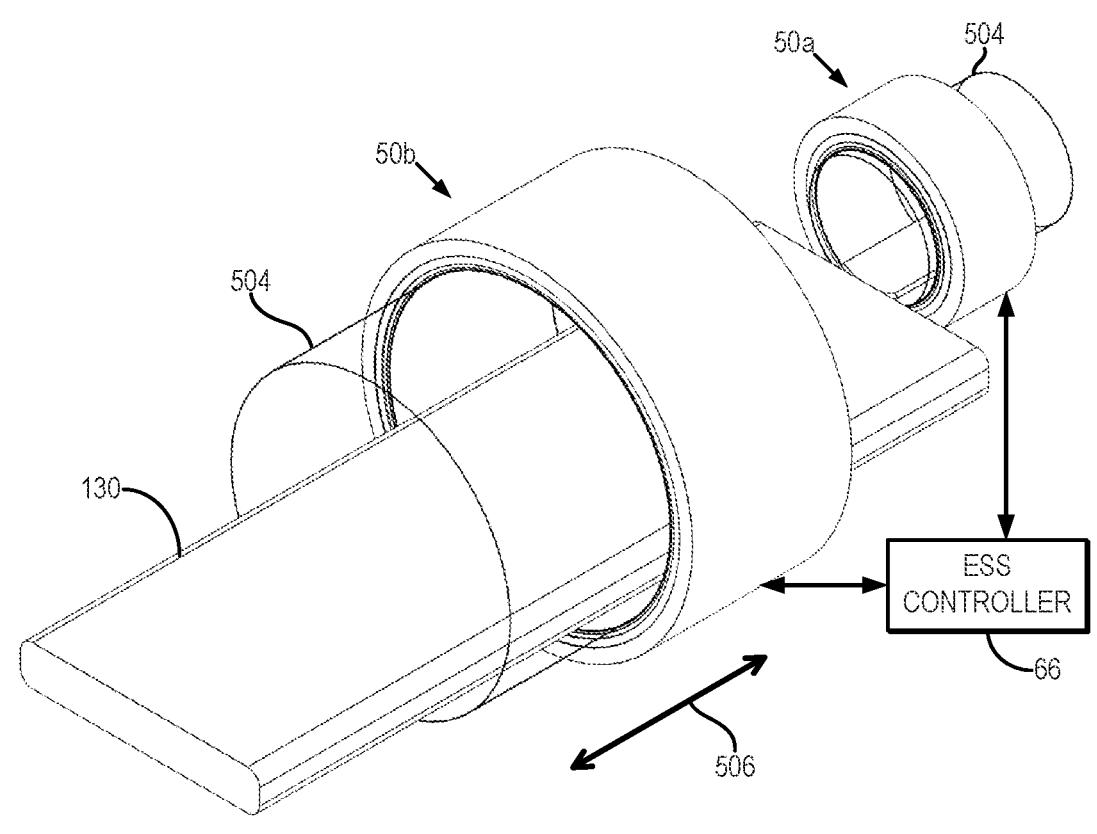
FIG. 5A
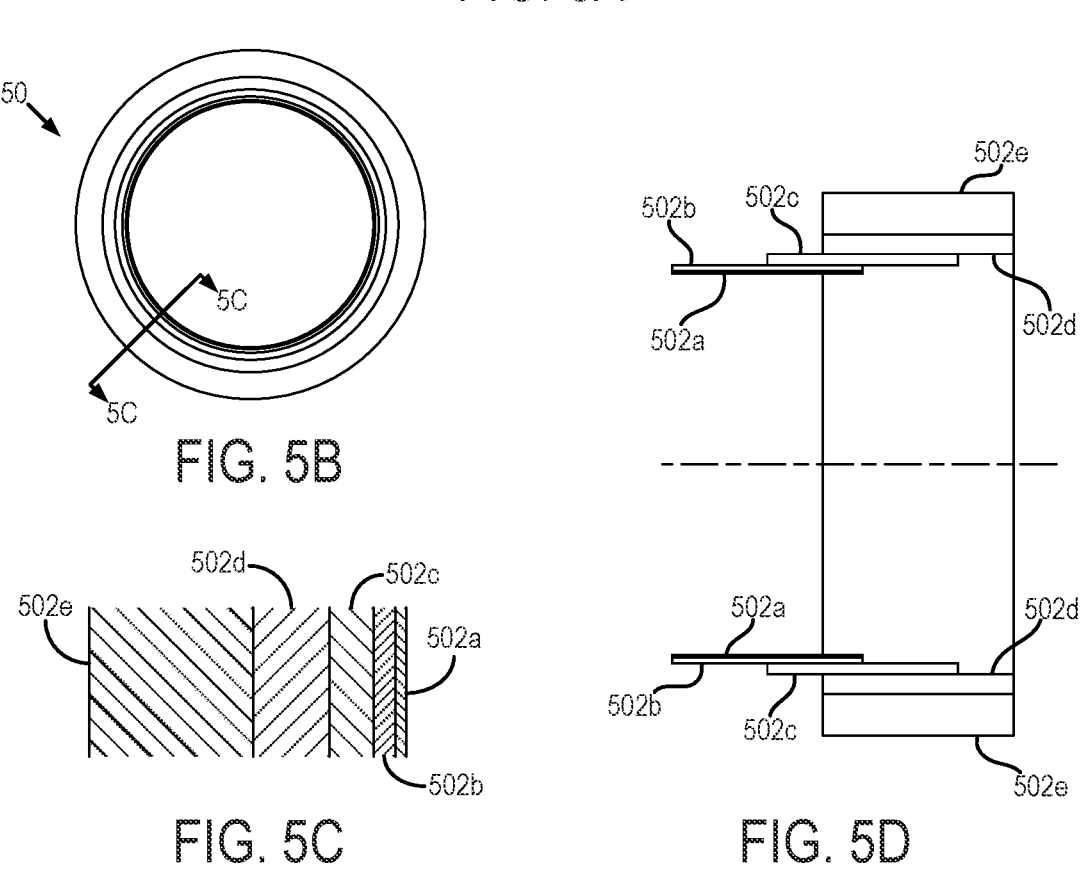
FIG. 5B
FIG. 5C
FIG. 5D

DOWNSTREAM VARIABLE THICKNESS ENERGY SELECTION SYSTEM FOR CHARGED PARTICLE THERAPY

CROSS-REFERENCE TO RELATED APPLICATIONS

This application represents the national stage entry of PCT/US2021/040358 filed on Jul. 2, 2021 and claims the benefit of U.S. Provisional Patent Application Ser. No. 63/106,266, filed on Oct. 27, 2020, and entitled "DOWNSTREAM VARIABLE THICKNESS ENERGY SELECTION SYSTEM FOR CHARGED PARTICLE THERAPY," the contents of which are herein incorporated by reference in its entirety.

BACKGROUND

Ion therapy (e.g., protons, helium, and carbon) has evolved to a highly sophisticated treatment delivery where Bragg peaks are deposited in the tumor volume. The range of the Bragg deposition depends on the ion's kinetic energy and is controlled by several different methods. It is undesirable to have long treatment times because the patient is required to be immobilized to ensure high quality treatment and long treatment times reduce overall efficiency for this limited resource.

In current charged particle therapy systems, an ion beam is generated and accelerated (i.e., its energy is increased) in an ion accelerator (e.g., a cyclotron, linac, or synchrotron). If the energy of the accelerated ion beam is not the desired energy then it is modified by an energy selection system ("ESS") at the ion accelerator and then transported using magnets to the patient.

Some of the current technical limitations for charged particle therapy to achieve a sufficiently high dose rate to the clinical tumor volume include the inability to quickly change energy levels (i.e., range), the inability to achieve a high ion beam current at every desired energy level, and the inability to access shallow ranges (e.g., 0-4 cm) without the use of a secondary device. Changing the energy of the ion beam at the ion accelerator requires the beam transport magnets to also be adjusted in order to account for the change in ion beam energy, which is both time and cost prohibitive. The magnet switching time limits the energy switching time and requires additional technology to allow the magnet to switch their field strength. In addition, changing the energy of the ion beam at the ion accelerator can produce unwanted radiation that must be attenuated for radiation safety purposes.

Active scanning techniques, such as pencil-beam scanning, for charged particle therapy provide additional challenges for efficient energy selection. One such barrier for adoption of scanned pencil beam particle therapy is the increased cost over conventional radiation therapy. One large factor in this cost is the expense and complexity needed to produce and transport various energies from the accelerator to the patient. Another large cost is the facility needed for a charged particle device. Such facilities require walls that are sufficiently thick to meet radiation safety standards. The facilities also require a much larger footprint than conventional radiation therapy facilities.

Although ion beam energy can be varied at the nozzle using, for example, a range modulator ("RM") wheel, this solution is not practical for use with pencil-beam scanning. For example double scatter systems use an RM wheel to modulate the pencil beam only on the central axis. Scattering devices placed downstream from the RM wheel are then used to spread the spot over the full field size, which then has to be collimated down to the field size needed. Such a configuration is not practical for pencil-beam scanning over a large field size because the necessary RM wheel would be prohibitively large. This configuration would also result in undesirable levels of spreading in the spot size of the ion beam.

SUMMARY OF THE DISCLOSURE

The present disclosure addresses the aforementioned drawbacks by providing an energy selection system for use in a charged particle therapy system. The energy selection system includes a variable thickness absorber that is configured to be housed within a nozzle of the charged particle therapy system and operable to adjust its thickness along a beam axis of the charged particle therapy system in order to change the energy of an ion beam passing through the variable thickness absorber. The variable thickness absorber accommodates up to the full treatment field size of the particle therapy system and does not operate only on central axis. In addition, the variable thickness absorber can vary the thickness from zero up to the maximum range of the accelerator.

It is another aspect of the present disclosure to provide an energy selection system for use in a charged particle therapy system, which includes a gantry and an absorber coupled to the gantry. The gantry and/or absorber are moveable relative to an ion beam of the charged particle therapy system in order to change an energy of the ion beam passing through the absorber.

It is still another aspect of the present disclosure to provide an energy selection system for use in a charged particle therapy system, which includes a support and a plurality of concentric cylindrical tubes coupled to the support. Each concentric cylindrical tube is composed of an absorber and configured to be translated along an axial direction so as to move into an ion beam path of the charged particle therapy system. When moved into the ion beam path, each cylindrical tube changes an energy of an ion beam passing therethrough.

It is yet another aspect of the present disclosure to provide an energy selection system for use in a charged particle therapy system, which includes an annular enclosure and a reservoir. The annular enclosure has an internal volume and circumscribes a central bore that is sized to receive a portion of a patient therethrough. The annular enclosure is configured to be positioned within a beam path of an ion beam of the charged particle therapy system. The reservoir is configured to be positioned outside the beam path of the ion beam. The annular enclosure and the reservoir are fluidically coupled to define a closed fluid dynamic system that is filled with a liquid absorber. Varying a volume of the liquid absorber in the internal volume of the annular enclosure adjusts an absorber thickness along the beam path in order to change an energy of the ion beam passing therethrough.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

BRIEF DESCRIPTION OF THE DRAWINGS

FIGS. 5A-5D show an example downstream variable thickness energy selection system implementing a cylindrical PETS design that enables the energy selection system to be placed adjacent, and surrounding, the patient.

DETAILED DESCRIPTION

Figure 1A:
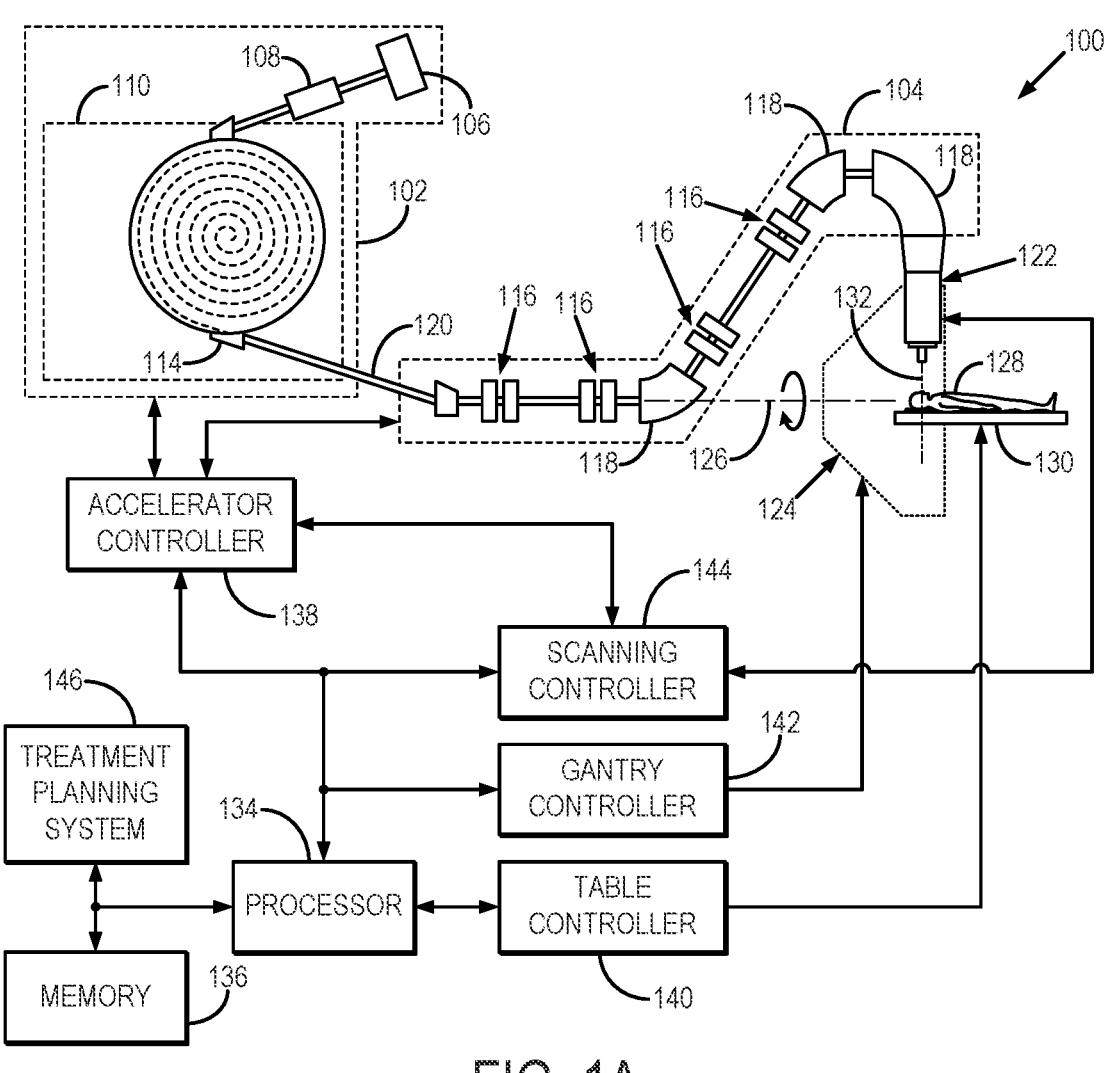
FIG. 1A shows an example charged particle therapy system, which can implement the downstream variable thickness energy selection systems described in the present disclosure.

Described here are variable thickness energy selection systems ("ESS") for use in a charged particle therapy system, such as a proton therapy system and/or an ion therapy (e.g., helium ion, carbon ion) therapy system. In general, the ESS described in the present disclosure includes a variable thickness ESS assembly, which is controllable to quickly and accurately vary the thickness of one or more absorbers (e.g., solid absorber, liquid absorber) that are positioned within the ion beam path, thereby allowing for rapid control of the energy selection of the ion beam. Advantageously, the ESS is housed within the beam delivery unit (e.g., the nozzle) of the ion therapy system and is, therefore, downstream of the charged particle generating system, the beam transport system, and the lateral beam shaping devices (e.g., scanning magnets).

The ESS described in the present disclosure is operable to adjust its thickness within clinically relevant times, such that the total energy of the ion beam can be quickly changed while maintaining a high beam current. As a result, overall treatment time can be reduced using the ESS described in the present disclosure.

Advantageously, the ESS is housed within the beam delivery unit (e.g., the nozzle) of the ion therapy system, such that energy selection is performed after all of the beam transport elements. As a result, there is no need for the charged particle generating system (e.g., the synchrotron, cyclotron, or accelerator) or those elements to be capable of producing or transporting a spectrum of various energies. This greatly simplifies the overall design of the charged particle generating system and beam transport system, including power supplies. Therefore, using the ESS described in the present disclosure allows for a significant reduction in the cost of equipment, as well as installation, commissioning, and maintenance costs while maintaining desired beam quality.

As another advantage, because energy selection is performed at the nozzle, the charged particle generating system is operable to generate a monoenergetic ion beam. Beam steering is therefore performed with a monoenergetic beam, which allows for a less complex beam steering control system to be used. Less complex beam steering control systems are safer and more economical.

As still another advantage of using the ESS described in the present disclosure, because no beam is lost upstream of the ESS, a high beam current is maintained.

Additionally, because no beam is lost upstream another advantage of the ESS described in the present disclosure is that the need for costly upstream shielding can be minimized.

The ESS described in the present disclosure can be arranged within the charged particle therapy system nozzle such that the dose monitor(s) and spot position monitor are upstream of the ESS. Thus, in some implementations, the highest energy beam can be generated to be incident on the dose monitor(s) and spot position monitor in order to minimize multiple scattering in the dose monitor(s) and/or spot position monitor for lower treatment energies, which can allow for better normal tissue sparing due to smaller spot sizes.

Because the ESS described in the present disclosure is housed within the nozzle of the charged particle therapy system, the need for a traditional range shifter within the nozzle can be eliminated. For instance, current charged particle therapy systems need range shifters that are usually 4-6 cm thick. The typical maximal range of charged particle therapy systems is 30 cm in water. Using the ESS described in the present disclosure, that range can be reduced to zero. In this way, the traditional range shifter used in a charged particle therapy system nozzle can be removed, further reducing the complexity and cost of the system. In addition, because the range can be modulated from the maximum of the accelerator down to zero without the need of secondary energy absorbers, the maximum energy of the accelerator may be reduced and, therefore, overall cost of the therapy system may be reduced.

As one non-limiting example, the high linear energy transfer ("LET") observed at the end of range for short range protons using traditional methods is significantly reduced when using the ESS described in the present disclosure. Thus, in these clinical applications the toxicities to normal tissues beyond the tumor can be reduced.

In proton therapy systems, the charged particle generating system can generally have a $dp/p$, less than 0.1%. In these instances, the range straggling and the spot size within the patient can be approximately constant for all treatment depths. As a result, the layer and spot spacing within the patient is independent of treatment depth, which therefore simplifies treatment planning optimization, eliminates the need for ridge filter type devices, and can minimize the overall treatment time.

In general, the energy selection systems described in the present disclosure provide a proximal to patient energy for treatment selection system ("PETS"), in which a variable thickness ESS is housed within the ion therapy nozzle, proximal to the patient. The ESS is operable to select (e.g., by reducing) the energy of the impinging ion beam before it is delivered to the patient. For example, the ESS can receive a monoenergetic ion beam that has been produced in an ion accelerator and transported to close proximity to the patient (e.g., within the nozzle of the ion beam therapy system) where the ESS modifies that energy to the one needed for the clinical treatment plan.

The ESS can be sized to cover the full field size (e.g., 40 cm×40 cm) of the charged particle therapy system, or a smaller field size as dictated by the prescribed radiation treatment plan, and designed such that it is operable at all gantry angles (e.g., full 360 degrees). In use, the ESS modifies the energy of the ion beam incident on the patient by changing the thickness of one or more absorbers contained within the ESS. By varying the thickness of the absorber(s), the range of the ion beam's Bragg peak can be shifted. Advantageously, the ESS is operable to vary the absorber thickness without human intervention. Further, this change in thickness can be done precisely and in rapid fashion.

The absorber in the ESS can be made from any suitable material that has the appropriate radiation properties that ensure consistent energy absorption per unit density, thermal characteristics that maintain quality under operational conditions, and mechanical dynamics that allow precise control of the variable thickness under high speed changes. In addition, the ESS can be dynamically positioned at different distances from the patient surface to allow for optimal spot size and patient clearance.

In some embodiments, the absorber can be composed of one or more solid materials. In some other embodiments, the absorber can be composed of one or more liquid materials. In these latter instances, the variable thickness ESS can be referred to as a liquid energy selection system ("LESS") that provides a variable thickness of liquid absorber in the beam path.

The LESS includes a closed system of liquid with two main components: a liquid range shifter ("LRS") and a range shifter reservoir ("RSR"). The LESS contains a liquid with appropriate radiation properties that ensures consistent energy absorption per unit density, thermal characteristics that maintain quality under operational conditions, and fluid dynamics that allow precise control of the variable thickness under high speed changes. For example, the LESS can contain a high density liquid with optimal viscosity and vapor pressure, and low reactivity properties, such as solutions containing lithium heteropolytungstate ("LST") or glycerol and related liquids. Liquid metals, such as mercury or gallium-based alloys, can also be used. In addition, because the LESS is composed of liquid, the lateral dimensions can be fixed to cover a large field size, such as 40 cm by 40 cm. Alternatively, the lateral dimensions can be variable, such as by having one or more differently sized LRSs that attach to the RSR, or the LRSs can have a dynamically changing lateral size. The ability to change the lateral size of the LRS allows for increased clearance if the LESS is positioned close to the patient surface.

Figure 1B:
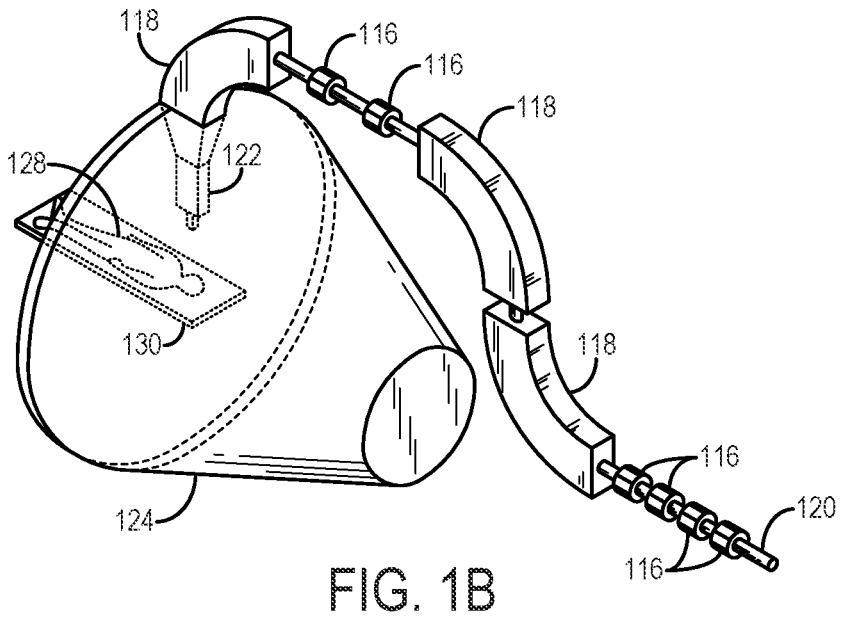
FIG. 1B shows a view of the gantry of the charged particle therapy system of FIG. 1A.

Referring now to FIGS. 1A and 1B, an example of a charged particle therapy system 100, which may be a proton beam therapy system, an ion beam therapy system, or the like, is illustrated. Examples of charged particles for use with a charged particle therapy system include protons, ions, and/or molecules containing such particles. For example, charged particle therapy may include proton therapy and/or ion therapy (e.g., helium ion, carbon ion). An example charged particle therapy system 100 generally includes a charged particle generating system 102 and a beam transport system 104. By way of example, the charged particle generating system 102 may include a cyclotron; however, in other configurations the charged particle generating system 102 may include a synchrotron, a synchrocyclotron, or other suitable accelerator.

The charged particle generating system 102 includes an ion source 106, an injector 108, and an accelerator 110, such as a cyclotron. As a non-limiting example, when the accelerator 110 is a cyclotron, the injector 108 can include an axial injector, a radial injector, or another suitable external injection system suitable for use with a cyclotron. As another non-limiting example, when the accelerator 110 is a synchrotron, the injector 108 can be a linear accelerator ("linac") or other suitable external injection system.

Ions generated in the ion source 106, such as hydrogen ions (i.e., protons), helium ions, or carbon ions, are accelerated by the injector 108 to form an ion beam that is injected into the accelerator 110. When the accelerator 110 is a cyclotron, the accelerator 110 can provide energy to the injected ion beam by way of a high frequency alternating voltage applied between two dees (e.g., D-shaped electrodes) inside a vacuum chamber. The dees are located between the poles of a large electromagnet that applied a static magnetic field perpendicular to the plane of the dees, which bends the ion beam into a circular trajectory within the vacuum chamber. When the alternating voltage is applied at the cyclotron resonance frequency of the particles in the ion beam, the ion beam is accelerated, which moves the ion beam path in an outward spiral trajectory while the particles in the ion beam are accelerated. When the accelerator 110 is a synchrotron, the accelerator 110 can provide energy to the injected ion beam by way of an acceleration cavity, where RF energy is applied to the ion beam. In the case of a synchrotron, quadrupole and dipole magnets are used to steer the ion beam about the accelerator 110 a number of times so that the ion beam repeatedly passes through the acceleration cavity.

After the energy of the ion beam traveling in the accelerator 110 has reached a preselected, desired energy level, which would typically be the optimized maximum energy (e.g., 250 MeV as a non-limiting example), the ion beam is extracted from the accelerator 110 through an extraction deflector 114. Extraction may occur by way of bumping, or kicking, the ion beam to an outer trajectory so that it passes through a septum, or by way of resonance extraction.

The beam transport system 104 includes a plurality of focusing magnets 116 and steering magnets 118. Examples of focusing magnets 116 include quadrupole magnets, and examples of steering magnets 118 include dipole magnets. The focusing magnets 116 and steering magnets 118 are used to contain the ion beam in an evacuated beam transport tube 120 and to deliver the high energy ion beam to a beam delivery device 122 that is situated in a treatment room. In some examples, the beam delivery device 122 may be referred to as a nozzle of the ion therapy system.

The beam delivery device 122 is coupled to a rotatable gantry 124 so that the beam delivery device 122 may be rotated about an axis of rotation 126 to delivery therapeutic radiation to a patient 128 positioned on a patient positioning device 130, which may be a patient table, a patient chair, or the like. The rotatable gantry 124 supports the beam delivery device 122 and deflection optics, including focusing magnets 116 and steering magnets 118, that form a part of the beam transport system 104. These deflection optics rotate about the rotation axis 126 along with the beam delivery device 122. Rotation of the rotatable gantry 124 may be provided, for example, by a motor (not shown in FIGS. 1A and 11). Alternatively, the beam delivery device 122 can be coupled to one or more fixed beams in one treatment room.

In this case, the patient is immobilized on a patient positioning device, such as a robotic chair or table.

Alternatively, the beam delivery device 122 may be coupled to a non-rotatable support in a fixed beam configuration. In such a configuration, the position of the patient positioning device (e.g., patient table or chair) 130 can be adjusted to move the patient relative to the ion beam.

In some configurations, the accelerator 110 provides an ion beam to a plurality of beam delivery devices located in different treatment rooms. In such configurations, the beam transport system 104 may connect to a series of switchyards that may include an array of dipole bending magnets that deflect the ion beam to any one of a plurality of deflection optics that each lead to a respective beam delivery device in the respective treatment room.

The beam delivery device 122 is designed to deliver precise dose distributions to a target volume within a patient. In general, an example beam delivery device 122 includes components that may either modify or monitor specific properties of an ion beam in accordance with a treatment plan. For instance, the beam delivery device 122 can include one or more dose monitors (e.g., a main dose monitor and a backup dose monitor). In use, the dose monitor(s) can monitor the dose of the impinging ion beam, and can trigger interlocks that stop beam delivery when deviations from prescribed values are observed. These dose monitors and their associated controls systems can be designed to measure very high beam currents from accelerators, such as cyclotrons, without loss of integrity.

The beam delivery device 122 may also, for example, include a device to spread or otherwise modify the ion beam position and profile, a dispersive element to modify the ion beam energy, and a plurality of beam sensors to monitor such properties. For example, scanning electromagnets may be used to scan the ion beam in orthogonal directions in a plane that is perpendicular to a beam axis 132. Advantageously, as described above the ESS described in the present disclosure are housed within the beam delivery device 122. Because the ESS is capable of selecting the desired energy of the ion beam, the range can be controlled and reduced without the need for a traditional range shifter ("RS") within the beam delivery device 122. When the beam delivery device 122 is configured for pencil beam-scanning ("PBS"), additional monitors can also be includes in the beam delivery device 122, such as beam profile and spot position monitors. In use, these monitors can trigger interlocks when the ion beam deviates from prescribed values.

The charged particle therapy system 100 is controlled by a central controller that includes a processor 134 and a memory 136 in communication with the processor 134. An accelerator controller 138 is in communication with the processor 134 and is configured to control operational parameters of the charged particle generating system 102, including the accelerator 110 and the beam transport system 104. A table controller 140 is in communication with the processor 134 and is configured to control the position of the patient positioning device (e.g., patient table or chair) 130. A gantry controller 142 is also in communication with the processor 134 and is configured to control the rotation of the rotatable gantry 124. A scanning controller 144 is also in communication with the processor and is configured to control the beam delivery device 122. The memory 136 may store a treatment plan prescribed by a treatment planning system 146 that is in communication with the processor 134 and the memory 136, in addition to control parameters or instructions to be delivered to the accelerator controller 138, the table controller 140, the gantry controller 142, and the scanning controller 144. The memory 136 may also store relevant patient information that may be utilized during a treatment session.

Before the ion beam is provided to the patient 128, the patient 128 is positioned so that the beam axis 132 intersects a treatment volume in accordance with a treatment plan prescribed by a treatment planning system 146. The patient 128 is positioned by way of moving the patient positioning device (e.g. patient table or chair) 130 into the appropriate position. The patient positioning device (e.g., patient table or chair) 130 position is controlled by the table controller 140, which receives instructions from the processor 134 to control the position of the patient positioning device (e.g., patient table or chair) 130. The rotatable gantry 124 is then set to a position dictated by the treatment plan so that the ion beam will be provided to the appropriate treatment location in the patient 128. The rotatable gantry 124 is controlled by the gantry controller 142, which receives instructions from the processor 134 to rotate the rotatable gantry 124 to the appropriate position. As indicated above, the position of the ion beam within a plane perpendicular to the beam axis 132 may be changed by the beam delivery device 122. The beam delivery device 122 is instructed to change this scan position of the ion beam by the scanning controller 144, which receives instruction from the processor 134. For example, the scanning controller 144 may control scanning electromagnets located in the beam delivery device 122 to change the scan position of the ion beam.

It is an advantage of the energy selections systems 50 described in the present disclosure that, because energy selection can be provided close to the patient, the construction of the charged particle therapy system can be made more compact and/or less expensive.

As one example, a cyclotron can be used to generate a monoenergetic beam. In this setup, a degrader is commonly required in the beamline in order to change the beam energy before it reaches the beam delivery device. Using the energy selections systems described in the present disclosure, a degrader is no longer needed when extracting a monoenergetic beam from a cyclotron.

As another example, the building shielding can be designed to allow for beam transport at a single energy level, such that reduced complexity and/or expense in the building shielding design can be realized.

As yet another example, the beam line components can be made simpler since the charged particle therapy system can include an accelerator that generates a monoenergetic beam of the same energy in each use. As a result, the beam line components can be designed and constructed to account for only that single energy level, reducing their complexity and cost.

Figure 2:
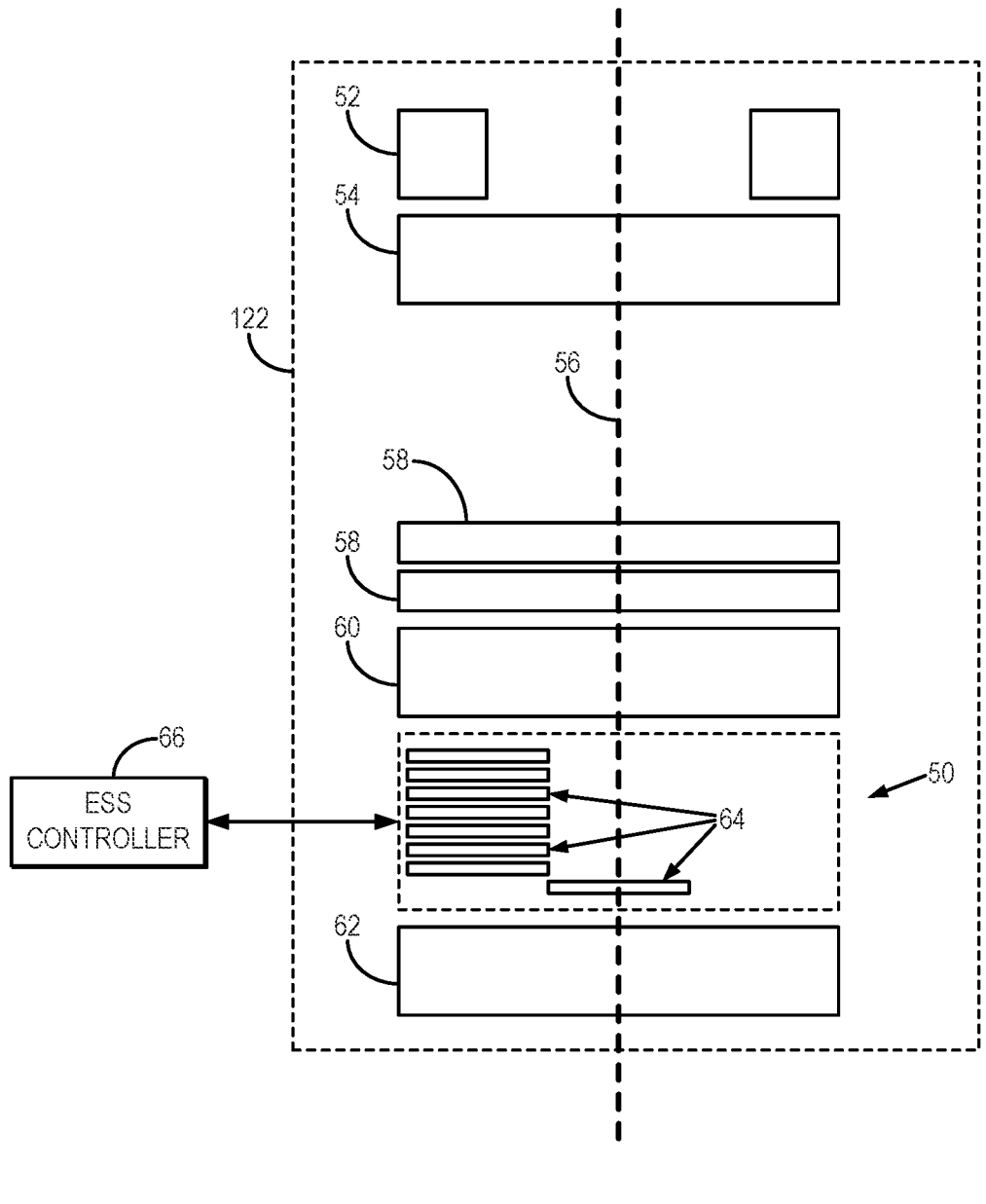
FIG. 2 shows an example downstream variable thickness energy selection system implementing a proximal to patient energy for treatment selection system ("PETS") design, in which the effective thickness of the energy selection system is varied by moving solid absorbers into and out of the beam path.

Referring now to FIG. 2, an example beam delivery device 122 that includes an energy selection system 50 according to some embodiments of the present disclosure is shown. In these embodiments, the energy selection system 50 implements a proximal to patient energy for treatment selection system ("PETS") design, in which the effective thickness of the energy selection system 50 is varied by moving one or more solid absorbers into and out of the beam path of the ion beam 56. Preferably, the solid absorbers are composed of a high-density material and are, therefore, high-density absorbers.

The beam delivery device 122, which may be referred to as a nozzle, of the ion therapy system can be configured for active beam scanning (e.g., pencil-beam scanning), such that the beam delivery device 122 includes a first scanning magnet 52 and a second scanning magnet 54 for laterally scanning the ion beam 56. For example, the first scanning magnet 52 can scan the ion beam 56 in the y-direction and the second scanning magnet 54 can scan the ion beam 56 in the x-direction. One or more dose monitors 58, a spot position monitor 60, and a ridge filter 62 can also be housed within the beam delivery device 122. The energy selection system 50 can be arranged downstream from the dose monitor(s) 58 and the spot position monitor 60, but upstream or downstream from the optional ridge filter 62 if desired, or the dose monitor(s) 58, spot position monitor 60, and/or optional ridge filter 62 may be integrated into the energy selection system 50. Advantageously, the energy selection system 50 allows for the high energy ion beam 56 to be generated from the accelerator 110, which together with the energy selection system 50 being located proximal to the patient a small spot size for treatment can be maintained even after the ion beam 56 passes through the energy selection system 50.

In some embodiments, the overall dimension of the energy selection system 50 along the beam axis 132 (e.g., the z-direction) can be less than 30 cm when using a suitable high density material construction for the energy selection system 50. For example, the physical maximal length in the z-direction of the energy selection system 50 can be as small as 2 to 5 cm and up to 30 cm along the beam axis 132. In some non-limiting examples, the physical maximal length in the z-direction of the energy selection system 50 can be 2 cm, 5 cm, or 10 cm. The physical size will generally depend on the radiologic properties of the material construction of the energy selection system 50.

In the example shown in FIG. 2, the energy selection system 50 is a mechanically operable system whose effective thickness can be varied by moving one or more solid absorbers 64 into the beam path of the ion beam 56. The one or more solid absorbers 64 are preferably composed of a suitable high-density material with favorable scattering properties (e.g., scattering properties that minimize or otherwise reduce lateral scattering of the ion beam 56 as it passes through the solid absorber(s) 64) and, therefore, can be referred to as high-density solid absorbers.

As one non-limiting example, the absorber(s) 64 can be composed of a suitable material that has the appropriate radiation properties to ensure consistent energy absorption per unit density, has thermal characteristics that maintain quality under operational conditions, and has mechanical dynamics that allow precise control of the variable thickness under high speed changes. In general, the absorber(s) 64 can be composed of plastics, metals, metal containing alloys, carbon-containing materials, or other suitable materials. Example plastics can include poly(methyl methacrylate) ("PMMA") materials, such as plexiglass or Lucite; Acrylonitrile butadiene styrene ("ABS") materials; polycarbonate materials, such as Lexan; polyethylene materials; polystyrene materials; and so on. Example carbon-containing materials can include elemental carbon materials, such as graphite, and carbon-containing compounds, such as carbides. As one example, a suitable carbon-containing compound can be boron carbide. Additionally or alternatively, the absorber(s) 64 can be composed of other suitable solid materials, such as wax.

In general, the absorber(s) 64 have a generally flat shape, such as a sheet, a slab, a plate, or the like. Each absorber 64 can be composed of the same material, or alternatively different absorbers 64 can be composed of different materials. Likewise, each absorber 64 can have the same thickness, or alternatively different absorbers 64 can have different thicknesses. By constructing the energy selection system 50 to have absorbers 64 with different thicknesses and composed of different materials, a wide range of possible energy selection states can be generated depending on the combination of absorber 64 thickness and materials that are positioned within the beam path.

The absorber(s) 64 can be moved into the beam path of the ion beam 56 under mechanical control, such as using a pneumatic system that pushes and pulls the absorber(s) 64 into and out of the beam path. Alternatively, the absorber(s) 64 can be moved into and out of the beam path of the ion beam 56 using other mechanical and/or dynamic systems, such as a series of actuators, stepper motor, and/or servos.

The energy selection system 50 can be controlled by an energy selection system ("ESS") controller 66 that is operable in response to instructions received from the processor 134 to control the operation of the energy selection system 50. For instance, the ESS controller 66 can operate the mechanical and/or dynamic systems that move the absorber(s) 64 into and out of the beam path. In use, the absorber(s) 64 are moved into and out of the beam path in order to adjust the energy of the ion beam 56 to a desired energy level at the exit of the energy selection system 50. The effective thickness of the energy selection system 50 in the PETS implementation can be varied under control of the ESS controller 66 according to a prescribed radiation treatment plan.

Figure 3:
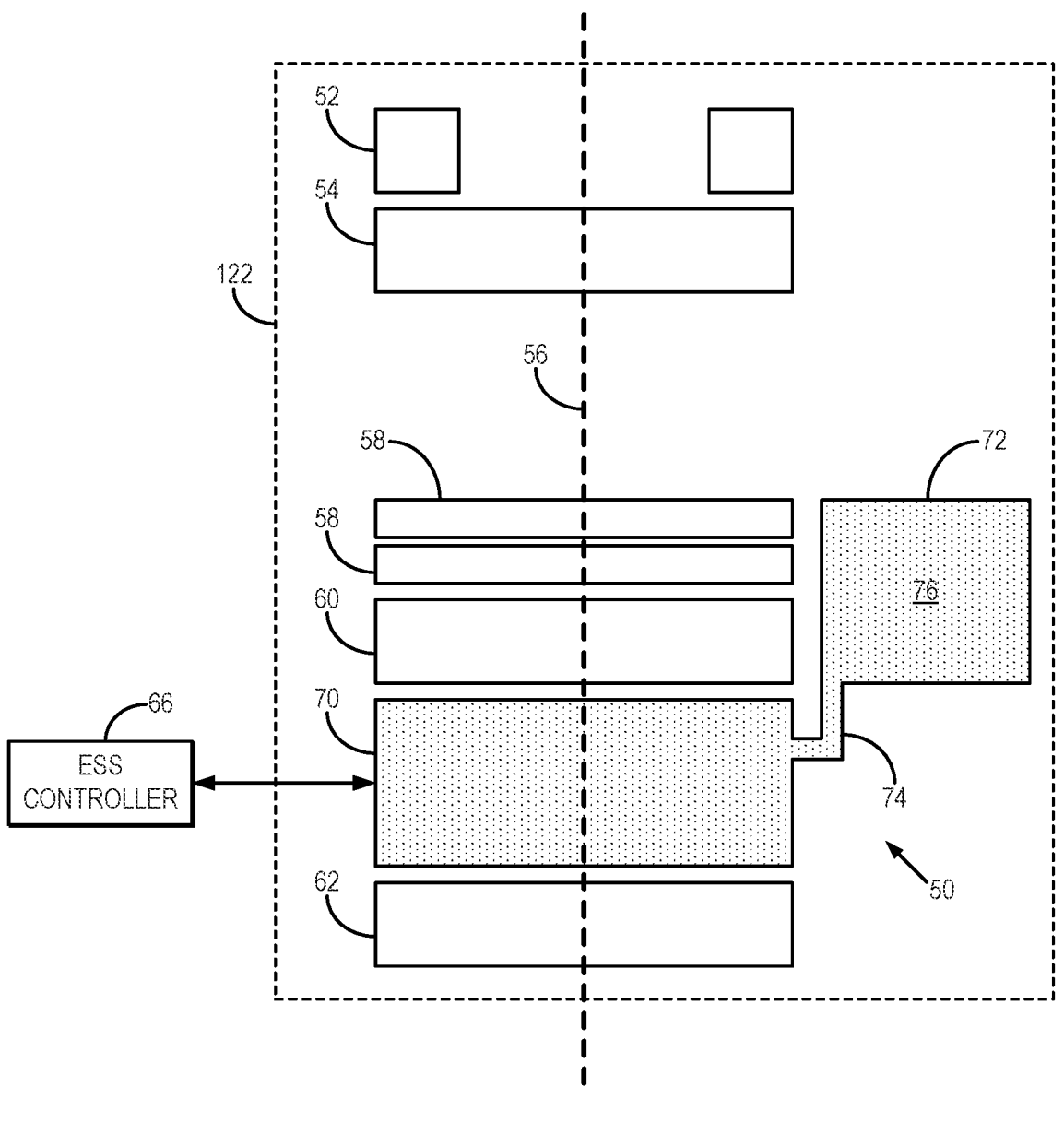
FIG. 3 shows an example downstream variable thickness energy selection system implementing a liquid energy selection system ("LESS") design, in which the effective thickness of the energy selection system is varied by changing the volume of liquid absorber in an enclosure of a closed fluid dynamic system, where the enclosure is positioned in the beam path.

Referring now to FIG. 3, another example beam delivery device 122 that includes an energy selection system 50 according to some embodiments of the present disclosure is shown. In these embodiments, the energy selection system 50 implements a liquid energy selection system ("LESS") design, in which the thickness of a liquid absorber positioned within the beam path of the ion beam 56 is varied under control of an ESS controller 66.

The beam delivery device 122, which may be referred to as a nozzle, of the ion therapy system can be configured for active beam scanning (e.g., pencil-beam scanning), such that the beam delivery device 122 includes a first scanning magnet 52 and a second scanning magnet 54 for laterally scanning the ion beam 56. As with the PETS embodiment illustrated in FIG. 2, the LESS embodiment of the energy selection system 50 can be arranged downstream from the dose monitor(s) 58 and the spot position monitor 60, but upstream from the optional ridge filter 62, or the dose monitor(s) 58, the spot position monitor 60, and/or the optional ridge filter 62 can be integrated into the structure of the LESS implementation of the energy selection system 50.

In the LESS implementation, the energy selection system 50 is constructed as a closed fluid dynamic system having a liquid range shifter ("LRS") enclosure 70 that is fluidically coupled to a reservoir 72, which may be referred to as a range shifter reservoir ("RSR"). As one example, the LRS enclosure 70 and the reservoir 72 can be fluidically coupled via a suitable fluid connection 74, which may include one or more tubes, pipes, or the like. This allows the position and shape of the reservoir 72 to be optimally designed for minimal impact on the treatment space (e.g., by minimizing interference with an imaging system or patient clearance zone). In some embodiments, the overall dimension of the LRS enclosure 70 along the beam axis 132 (e.g., the z-direction) can be less than the maximum penetration depth in water for the beam. For example, by using a high density liquid absorber, the physical size of the LRS enclosure 70 can be less than the maximum penetration depth in water for the beam along the beam axis 132, such as 2 cm, 5 cm, or 10 cm.

The reservoir 72 is filled with a liquid absorber 76, which as described above includes liquid or other fluid that has appropriate radiation properties that ensures consistent energy absorption per unit density, has thermal characteristics that maintain quality under operational conditions, and has fluid dynamics that allow precise control of the variable thickness under high speed changes. For example, the liquid absorber 76 can be a high-density liquid with optimal viscosity and vapor pressure, and low reactivity properties. As one non-limiting example, the liquid absorber 76 can include a solution containing lithium heteropolytungstate ("LST") or a solution containing a high proportion of hydrogen, such as glycerol and related liquids. Alternatively, the liquid absorber 76 can include liquid metals, such as mercury or gallium-based alloys.

The liquid absorber 76 can be moved into and out of the LRS enclosure 70, such as by mechanical retraction and expansion or other fluidic control. The change in thickness can be accomplished by allowing the thickness of the LRS enclosure to mechanically change. Thus, in general, the LRS enclosure 70 is an expandable enclosure whose shape can change as the volume of the liquid absorber 76 within the enclosure 70 is changed. As one non-limiting example, the enclosure 70 can have bellowed side walls, such that as the volume of the liquid absorber 76 is increased within the enclosure 70 the side walls will expand to adjust the thickness of the enclosure 70 along the beam axis 132 direction, thereby accommodating the increased volume of liquid absorber 76. Similarly, by removing liquid absorber 76 from the enclosure to reduce its volume the side walls would retract, thereby reducing the thickness of the enclosure 70.

In use, the mechanical expansion and retraction of the volume of the LRS enclosure 70 can be controlled under instructions from the ESS controller 66 to adjust the thickness of the enclosure 70 by changing the volume of the liquid absorber 76 in the LRS enclosure 70. Because the energy selection system 50 in the LESS implementation is constructed as a closed system, changing the volume of liquid absorber 76 in the enclosure 70 by moving liquid absorber 76 into the enclosure 70 from the reservoir 72 will increase the amount of liquid absorber 76 in the enclosure 70. In this way, the amount of liquid absorber 76 through which the ion beam 56 passes can be varied very rapidly, thereby allowing for an energy selection of the ion beam 56 by controlling the thickness of the enclosure 70. The change in energy selection (i.e., range selection) can be very small, such that the change can practically be a continuous change in range while the ion beam is continuously on. As one non-limiting example, the change in volume of the enclosure 70 can be accomplished by allowing the width of the enclosure 70 to mechanically change with bellowed end walls while maintaining a constant wall height.

The energy selection system 50 can be controlled by the ESS controller 66 that is operable in response to instructions received from the processor 134 to control the operation of the energy selection system 50. For instance, the ESS controller 66 can operate the fluidic systems that move the liquid absorber 76 into and out of the LRS enclosure 70. In use, liquid absorber 76 is moved into and out of the LRS enclosure 70 in order to adjust the thickness of liquid absorber 76 positioned within the beam path, thereby adjusting the energy of the ion beam 56 to a desired energy level at the exit of the energy selection system 50. The effective thickness of the energy selection system 50 in the LESS implementation can be varied under control of the ESS controller according to a prescribed radiation treatment plan.

The ESS controller 66 can dynamically position the reservoir 72 at different distances relative to the patient surface in order to allow for optimal spot size and patient clearance. In addition, because the LESS is composed of liquid, the lateral dimensions can be fixed to cover a large field size, such as 40 cm by 40 cm. Alternatively, the lateral dimensions can be variable, such as by having one or more differently sized LRS enclosures 70 that attach to the reservoir 72, or the LRS enclosure(s) 70 can have a dynamically changing lateral size. The ability to change the lateral size of the LRS enclosure 70 allows for increased clearance if the LESS energy selection system 50 is positioned close to the patient surface.

In the examples described above, the energy selection systems are shown with a generally planar configuration. In other embodiments, the energy selection systems, whether a PETS implementation or a LESS implementation, may be configured in other geometries. For example, the energy selection system can have a generally cylindrical configuration. Advantageously, in the cylindrical geometry, the energy selection system can be arranged adjacent and surrounding the patient or a portion thereof. This allows for the energy selection system to be remote to the beam delivery device, thereby simplifying the design and hardware used for the charged particle therapy system. Moreover, the cylindrical design allows for 360 degrees of coverage around the patient, or portion thereof, such that the energy selection system 50 can remain in position while the ion beam is repositioned around the patient, or while the patient is repositioned relative to the ion beam.

Figures 4A, 4B:
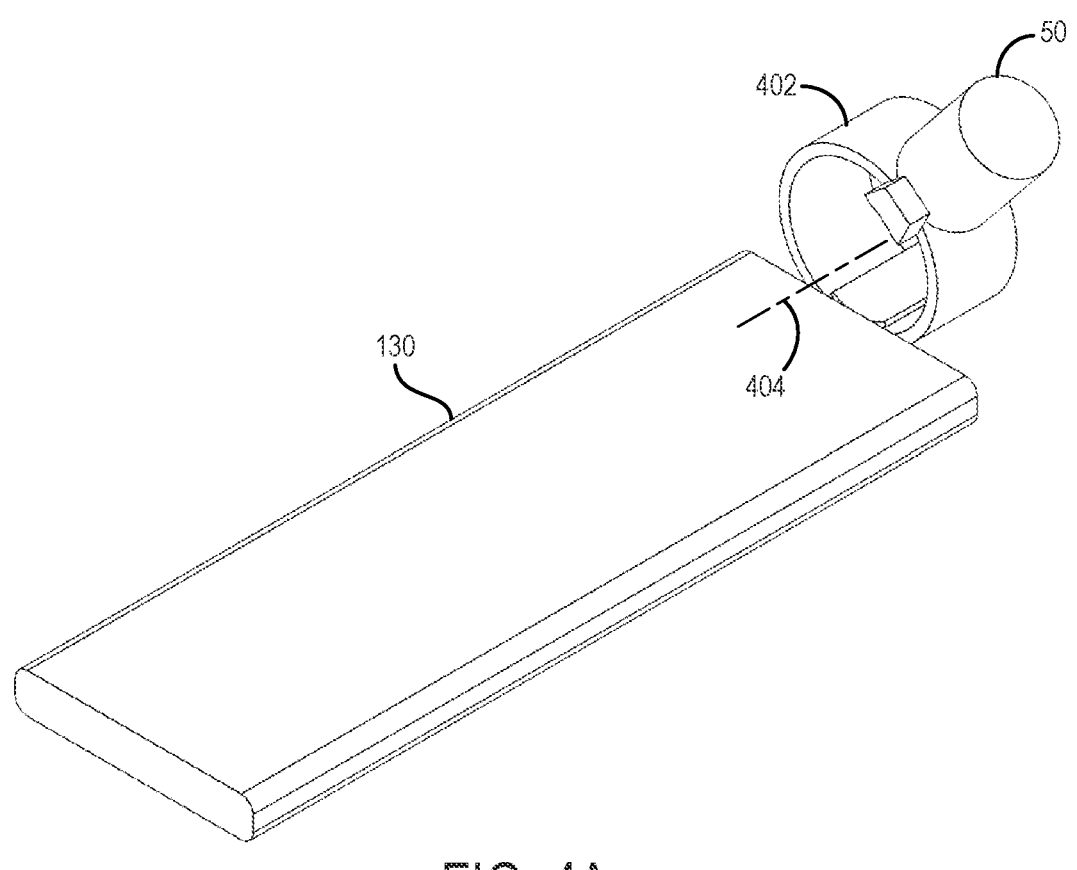
FIGS. 4A and 4B show an example downstream variable thickness energy selection system implementing a gantry mounted design that enables the energy selection system to be placed adjacent, and surrounding, the patient.

Referring now to FIGS. 4A and 4B, in one implementation an energy selection system 50 can be mounted or otherwise coupled to an annular support 402. The annular support 402 may define, for instance, a gantry that supports the energy selection system 50 and permits movement of the energy selection system 50 around a patient. The annular support 402 may be sized to surround a patient or a portion thereof. For example, as shown in FIG. 4A, the annular support 402 may be sized to surround a patient's head. In other instances, the annular support 402 may be sized to surround a patient's torso.

In some embodiments, the energy selection system 50 is moveably coupled to the annular support 402, such that the energy selection system 50 can be moved into different positions around the patient without moving the annular support 402. As an example, the energy selection system 50 may be movably coupled to the annular support 402 via a track, or the like, that allows for the energy selection system 50 to be slid around the periphery of the annular support 402 into different angular positions around a central axis 404 of the annular support 402. Additionally or alternatively, the annular support 402 can be rotatable, translatable, or otherwise moveable around the patient. For instance, the annular support 402 can be rotated through different angular positions while keeping the energy selection system 50 fixed, such that the energy selection system 50 is caused to rotate through the different angular positions.

The energy selection system 50 may be a variable thickness energy selection system, such as a PETS or LESS based energy selection system. Alternatively, the energy selection system 50 may have a constant thickness. In some implementations, more than one energy selection system 50 may be mounted or otherwise coupled to the annular support 402, such that different energy selection systems 50 can be moved into and out of the ion beam in order to provide different energy selection of the ion beam. For instance, two different energy selection systems 50 may be mounted or otherwise coupled to the annular support 402, such as a first energy selection system 50 with a first constant thickness (or range of variable thicknesses) to provide a first level of energy selection (or range of energy selections), and a second energy selection system 50 with a second constant thickness (or range of variable thicknesses) to provide a second level of energy selection (or range of energy selections).

The energy selection system 50 can be controlled by an ESS controller 66 that is operable in response to instructions received from the processor 134 to control the operation of the energy selection system 50. For instance, the ESS controller 66 can operate the mechanical and/or dynamic systems that move energy selection system 50 and/or annular support 402 such that the energy selection system 50 is moved into and out of the beam path in order to adjust the energy of the ion beam 56 to a desired energy level at the exit of the energy selection system 50. The effective thickness of the energy selection system 50 in the PETS and LESS implementations can be varied under control of the ESS controller 66 according to a prescribed radiation treatment plan.

Referring now to FIGS. 5A-5D, in some implementations an energy selection system 50 can be configured as a PETS energy selection system 50 in a cylindrical geometry. For example, an energy selection system 50 can include a plurality of concentric cylindrical tubes 502 that can be moved into and out of the ion beam path to provide energy selection. The energy selection system 50 may be sized to surround a patient or a portion thereof. For example, as shown in FIG. 5A, the energy selection system may be sized to surround a patient's head (e.g., energy selection system 50a), or to surround a patient's torso (e.g., energy selection system 50b).

The cylindrical tubes 502 can each have different thicknesses, the same thickness, or combinations thereof. As a non-limiting example, as shown in FIGS. 5B-5D, the energy selection system 50 includes a plurality of cylindrical tubes 502 that each have a different thickness. In this particular example, the energy selection system 50 includes five cylindrical tubes 502a, 502b, 502c, 502d, 502e, each having a different thickness. Additionally or alternatively, each cylindrical tube 502 can have different material properties, the same material properties, or the plurality of cylindrical tubes 502 can include a combination of tubes having the same and different material properties.

In general, the cylindrical tubes 502 can be composed of a suitable high-density material with favorable scattering properties (e.g., scattering properties that minimize or otherwise reduce lateral scattering of the ion beam 56 as it passes through the cylindrical tube(s) 502) and, therefore, can be referred to as high-density solid absorbers. As one non-limiting example, the cylindrical tubes 502 can be composed of a suitable material that has the appropriate radiation properties to ensure consistent energy absorption per unit density, has thermal characteristics that maintain quality under operational conditions, and has mechanical dynamics that allow precise control of the variable thickness under high speed changes. In general, the cylindrical tubes 502 can be composed of plastics, metals, metal containing alloys, carbon-containing materials, or other suitable materials. Example plastics can include poly(methyl methacrylate) ("PMMA") materials, such as plexiglass or Lucite; Acrylonitrile butadiene styrene ("ABS") materials; polycarbonate materials, such as Lexan; polyethylene materials; polystyrene materials; and so on. Example carbon-containing materials can include elemental carbon materials, such as graphite, and carbon-containing compounds, such as carbides. As one example, a suitable carbon-containing compound can be boron carbide. Additionally or alternatively, the cylindrical tubes 502 can be composed of other suitable solid materials, such as wax.

The cylindrical tubes 502 can be mounted or otherwise coupled to a support 504, which may be an annular gantry, a base cylindrical tube, or one or more linear supports that extend along the axial direction 506. In some instances, the support 504 is longer than the cylindrical tubes 502. The cylindrical tubes 502 are moveable (e.g., translatable) along, or over, the support 504. In some instances, the support 504 can include a cylindrical base that is concentrically nested within the innermost cylindrical tube 502. Alternatively, the support 504 can include one or more linear supports that extend along the axial direction 506 of the energy selection system 50 (e.g., the central axis 508 of the cylindrical tubes 502).

In use, the cylindrical tubes 502 can be translated along the axial direction 506 to move into and out of the ion beam in order to provide energy selection of the beam. As one example, one or more actuators can push and pull the cylindrical tubes 502 such that the cylindrical tubes 502 are made to translate along the axial direction 506. For instance, the innermost cylindrical tube 502 can be translated along, or over, the support 504, and each successively larger cylindrical tube 502 can be translated along, or over, the respectively adjacent inner cylindrical tube 502. Alternatively, the cylindrical tube(s) 502 can be moved into the beam path of the ion beam 56 under other types of mechanical control, such as using a pneumatic system that pushes and pulls the cylindrical tube(s) 502 into and out of the beam path. Alternatively, cylindrical tube(s) 502 can be moved into and out of the beam path of the ion beam 56 using other mechanical and/or dynamic systems, such as by using a stepper motor and/or servos.

The energy selection system 50 can be controlled by an ESS controller 66 that is operable in response to instructions received from the processor 134 to control the operation of the energy selection system 50. For instance, the ESS controller 66 can operate the mechanical and/or dynamic systems that move the cylindrical tubes 502 into and out of the beam path in order to adjust the energy of the ion beam 56 to a desired energy level at the exit of the energy selection system 50. The effective thickness of the energy selection system 50 in the PETS implementation can be varied under control of the ESS controller 66 according to a prescribed radiation treatment plan.

Figure 6A:
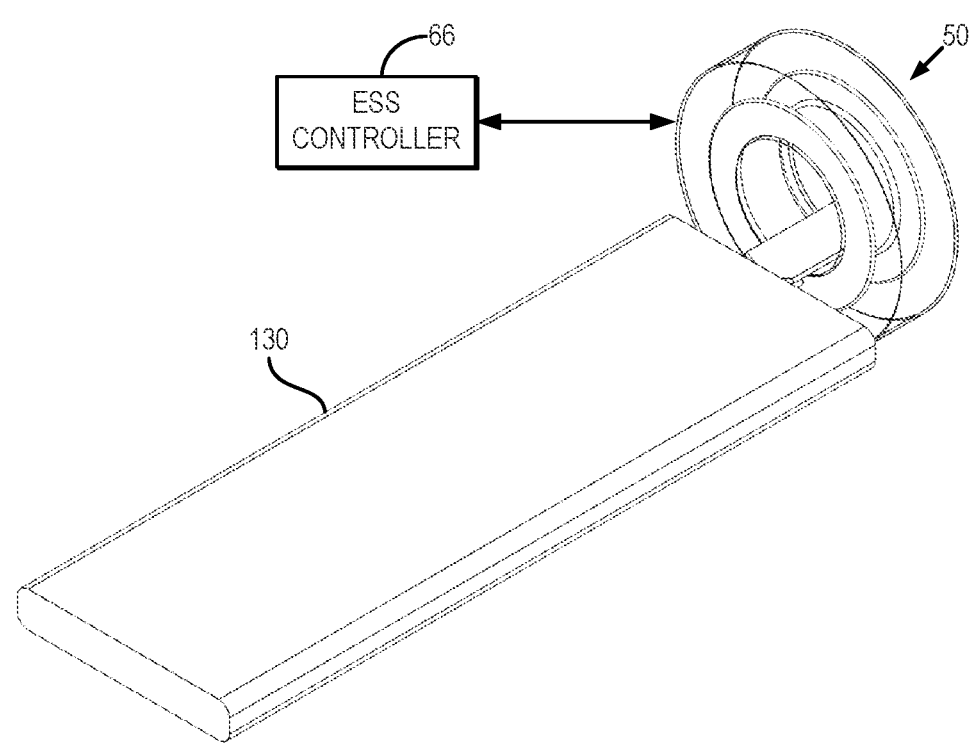
FIGS. 6A-6D shows an example downstream variable thickness energy selection system implementing a cylindrical LESS design that enables the energy selection system to be placed adjacent, and surrounding, the patient.
Figure 6B:
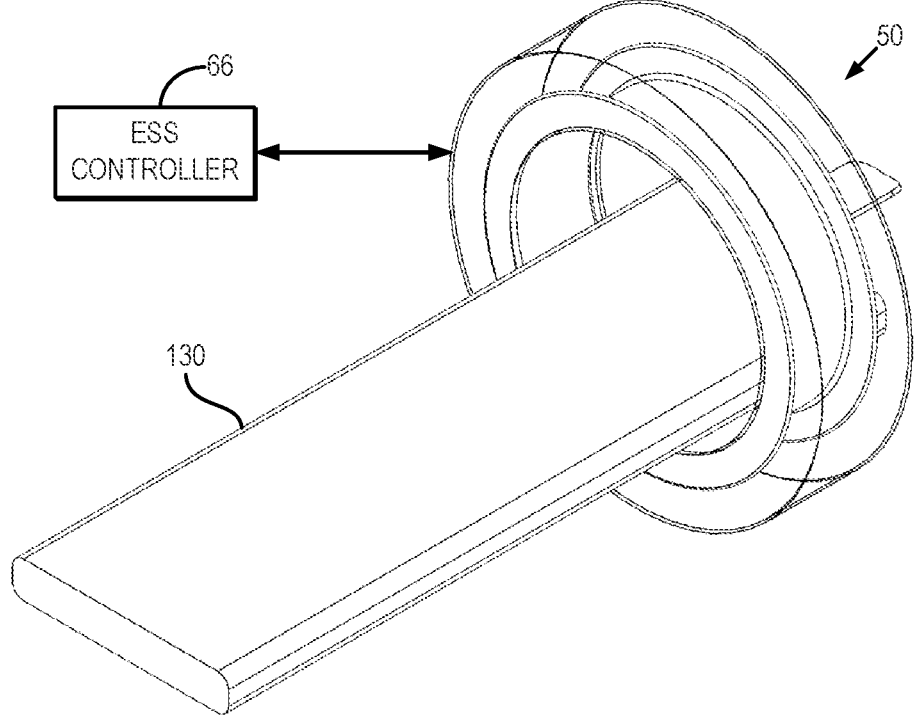

Referring now to FIGS. 6A-6D, in some implementations an energy selection system 50 can be configured as a LESS energy selection system 50 in a cylindrical geometry. The energy selection system 50 may be sized to surround a patient or a portion thereof. For example, as shown in FIG. 6A, the energy selection system may be sized to surround a patient's head, or as shown in FIG. 6B, may be sized to surround a patient's torso.

Figures 6C, 6D:
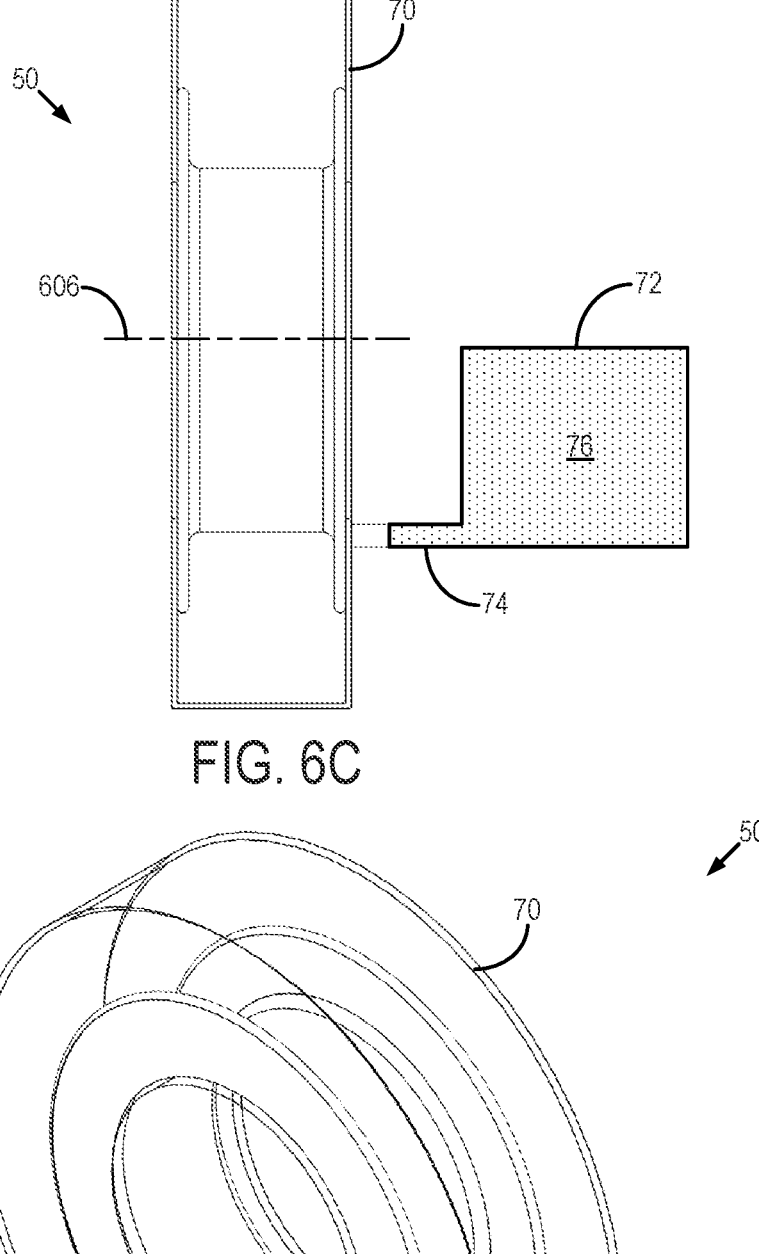

As shown in FIGS. 6C and 6D, the cylindrical LESS implementation of an energy selection system 50 can include a cylindrical annular LRS enclosure 70 that is fluidically coupled to a reservoir 72. As one example, the LRS enclosure 70 and the reservoir 72 can be fluidically coupled via a suitable fluid connection 74, which may include one or more tubes, pipes, or the like. The fluid connection 74 can fluidically couple the reservoir 72 to the LRS enclosure via an inlet 602 and an outlet 604, such that the liquid absorber 76 can be moved into and out of the LRS enclosure 70, such as by mechanical retraction and expansion or other fluidic control, via the inlet 602 and outlet 604, respectively.

The reservoir 72 is filled with a liquid absorber 76, which as described above includes liquid or other fluid that has appropriate radiation properties that ensures consistent energy absorption per unit density, has thermal characteristics that maintain quality under operational conditions, and has fluid dynamics that allow precise control of the variable thickness under high speed changes. For example, the liquid absorber 76 can be a high-density liquid with optimal viscosity and vapor pressure, and low reactivity properties. As one non-limiting example, the liquid absorber 76 can include a solution containing lithium heteropolytungstate ("LST") or a solution containing a high proportion of hydrogen, such as glycerol and related liquids. Alternatively, the liquid absorber 76 can include liquid metals, such as mercury or gallium-based alloys.

In use, the mechanical expansion and retraction of the volume of the LRS enclosure 70 can be controlled under instructions from an ESS controller 66 to adjust the thickness of the enclosure 70 by changing the volume of the liquid absorber 76 in the LRS enclosure 70. Because the energy selection system 50 in the LESS implementation is constructed as a closed system, changing the volume of liquid absorber 76 in the enclosure 70 by moving liquid absorber 76 into the enclosure 70 from the reservoir 72 will increase the amount of liquid absorber 76 in the enclosure 70. In this way, the amount of liquid absorber 76 through which the ion beam 56 passes can be varied very rapidly, thereby allowing for an energy selection of the ion beam 56 by controlling the thickness of the enclosure 70. The change in energy selection (i.e., range selection) can be very small, such that the change can practically be a continuous change in range while the ion beam is continuously on.

The energy selection system 50 can be controlled by the ESS controller 66 that is operable in response to instructions received from the processor 134 to control the operation of the energy selection system 50. For instance, the ESS controller 66 can operate the fluidic systems that move the liquid absorber 76 into and out of the LRS enclosure 70. In use, liquid absorber 76 is moved into and out of the LRS enclosure 70 in order to adjust the thickness of liquid absorber 76 positioned within the beam path, thereby adjusting the energy of the ion beam 56 to a desired energy level at the exit of the energy selection system 50. The effective thickness of the energy selection system 50 in the LESS implementation can be varied under control of the ESS controller according to a prescribed radiation treatment plan.

The ESS controller 66 can dynamically adjust the axial dimensions (i.e., dimensions along the central axis 606) of the cylindrical annular LRS enclosure 70. For instance, the axial dimensions can be variable, such as by having one or more differently sized LRS enclosures 70, or the LRS enclosure(s) 70 can have a dynamically changing axial size. The ability to change the axial size of the LRS enclosure 70 allows for increased clearance if the LESS energy selection system 50 is positioned close to the patient surface.

The present disclosure has described one or more preferred embodiments, and it should be appreciated that many equivalents, alternatives, variations, and modifications, aside from those expressly stated, are possible and within the scope of the invention.

The invention claimed is:

1. An energy selection system for use in a charged particle therapy system, comprising:

a variable thickness absorber configured to be housed within a nozzle of the charged particle therapy system and operable to adjust its thickness along a beam axis of the charged particle therapy system in order to change an energy of an ion beam passing through the variable thickness absorber;

wherein the variable thickness absorber is configured to be housed within the nozzle downstream a dose monitor and a spot position monitor; and wherein the variable thickness absorber is configured to be housed within the nozzle upstream a ridge filter.

2. The energy selection system of claim 1, wherein the variable thickness absorber is composed of a plurality of solid plates that are operable to move into and out of a beam path of the ion beam as the ion beam passes through the nozzle.

3. The energy selection system of claim 2, wherein each of the plurality of solid plates is composed of a same material.

4. The energy selection system of claim 2, wherein different ones of the plurality of solid plates are composed of different materials.

5. The energy selection system of claim 2, wherein each of the plurality of solid plates has a same thickness.

6. The energy selection system of claim 2, wherein different ones of the plurality of solid plates have different thicknesses.

7. The energy selection system of claim 2, wherein the plurality of solid plates are composed of a plastic.

8. The energy selection system of claim 7, wherein the plastic comprises one of poly(methyl methacrylate) (PMMA), acrylonitrile butadiene styrene (ABS), polycarbonate, polyethylene, or polystyrene.

9. The energy selection system of claim 2, wherein the plurality of solid plates are composed of a metal.

10. The energy selection system of claim 2, wherein the plurality of solid plates are composed of a carbon-containing material.

11. The energy selection system of claim 10, wherein the carbon-containing material comprises one of graphite or boron carbide.

12. The energy selection system of claim 2, further comprising an actuator that is configured to selectively move the plurality of solid plates into and out of the beam path of the ion beam in order to vary the thickness of the variable thickness absorber.

13. The energy selection system of claim 12, wherein the actuator comprises a pneumatic actuator.

14. The energy selection system of claim 1, wherein the variable thickness absorber comprises:

an enclosure configured to be positioned within a beam path of the ion beam as the ion beam passes through the nozzle;

a reservoir configured to be positioned outside the beam path of the ion beam as the ion beam passes through the nozzle; and wherein the enclosure and the reservoir are fluidically coupled to define a closed fluid dynamic system that is filled with a liquid absorber.

15. The energy selection system of claim 14, wherein the liquid absorber comprises a solution containing lithium heteropolytungstate (LST).

16. The energy selection system of claim 14, wherein the liquid absorber comprises a solution containing glycerol.

17. The energy selection system of claim 14, wherein the liquid absorber comprises a liquid metal.

18. The energy selection system of claim 17, wherein the liquid metal is one of mercury or a gallium-based alloy.

19. The energy selection system of claim 14, further comprising a pump that is operable to move the liquid absorber between the enclosure and the reservoir in order to change a volume of the liquid absorber in the enclosure, thereby varying the thickness of the variable thickness absorber.

20. The energy selection system of claim 1, wherein the variable thickness absorber is sized to have a maximum dimension along the beam axis less than 30 centimeters.

21. The energy selection system of claim 1, wherein the variable thickness absorber is configured to be housed within the nozzle with the dose monitor and/or spot position monitor and/or ridge filter is integrated into the energy selection system.

22. An energy selection system for use in a charged particle therapy system, comprising:
   a variable thickness absorber configured to be housed within a nozzle of the charged particle therapy system and operable to adjust its thickness along a beam axis of the charged particle therapy system in order to change an energy of an ion beam passing through the variable thickness absorber;
   wherein the variable thickness absorber comprises:
      an enclosure configured to be positioned within a beam path of the ion beam as the ion beam passes through the nozzle;
      a reservoir configured to be positioned outside the beam path of the ion beam as the ion beam passes through the nozzle; and
      wherein the enclosure and the reservoir are fluidically coupled to define a closed fluid dynamic system that is filled with a liquid absorber; and
      wherein a lateral dimension of the enclosure is operable to dynamically change a lateral size of the variable thickness absorber.

23. The energy selection system of claim 22, wherein the liquid absorber comprises a solution containing lithium heteropolytungstate (LST).

24. The energy selection system of claim 22, wherein the liquid absorber comprises a solution containing glycerol.

25. The energy selection system of claim 22, wherein the liquid absorber comprises a liquid metal.

26. The energy selection system of claim 25, wherein the liquid metal is one of mercury or a gallium-based alloy.

27. The energy selection system of claim 22, further comprising a pump that is operable to move the liquid absorber between the enclosure and the reservoir in order to change a volume of the liquid absorber in the enclosure, thereby varying the thickness of the variable thickness absorber.

28. An energy selection system for use in a charged particle therapy system, comprising:
   a variable thickness absorber configured to be housed within a nozzle of the charged particle therapy system and operable to adjust its thickness along a beam axis of the charged particle therapy system in order to change an energy of an ion beam passing through the variable thickness absorber;
   wherein the variable thickness absorber comprises:
      an enclosure configured to be positioned within a beam path of the ion beam as the ion beam passes through the nozzle;
      a reservoir configured to be positioned outside the beam path of the ion beam as the ion beam passes through the nozzle; and
      wherein the enclosure and the reservoir are fluidically coupled to define a closed fluid dynamic system that is filled with a liquid absorber; and
      wherein the liquid absorber comprises a solution containing lithium heteropolytungstate (LST).

29. An energy selection system for use in a charged particle therapy system, comprising:
   a variable thickness absorber configured to be housed within a nozzle of the charged particle therapy system and operable to adjust its thickness along a beam axis of the charged particle therapy system in order to change an energy of an ion beam passing through the variable thickness absorber;
   wherein the variable thickness absorber comprises:
      an enclosure configured to be positioned within a beam path of the ion beam as the ion beam passes through the nozzle;
      a reservoir configured to be positioned outside the beam path of the ion beam as the ion beam passes through the nozzle; and
      wherein the enclosure and the reservoir are fluidically coupled to define a closed fluid dynamic system that is filled with a liquid absorber; and
      wherein the liquid absorber comprises a solution containing glycerol.

* * * * *